United States Patent
Choi et al.

(10) Patent No.: US 10,881,333 B2
(45) Date of Patent: Jan. 5, 2021

(54) METHOD AND APPARATUS FOR PREDICTING IN VIVO ANALYTE CONCENTRATION USING LEARNING AND A NET ANALYTE SIGNAL

(71) Applicant: SAMSUNG ELECTRONICS CO., LTD., Suwon-si (KR)

(72) Inventors: Seonmyeong Choi, Suwon-si (KR); Jinyoung Park, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/270,812

(22) Filed: Sep. 20, 2016

(65) Prior Publication Data
US 2017/0079565 A1 Mar. 23, 2017

(30) Foreign Application Priority Data

Sep. 23, 2015 (KR) ........................ 10-2015-0134872

(51) Int. Cl.
| | | |
|---|---|---|
| *A61B 5/145* | (2006.01) | |
| *A61B 5/1495* | (2006.01) | |
| *A61B 5/1455* | (2006.01) | |
| *G01N 33/483* | (2006.01) | |
| *A61B 5/00* | (2006.01) | |
| *G16H 50/20* | (2018.01) | |
| *G01N 21/35* | (2014.01) | |

(52) U.S. Cl.
CPC ........ *A61B 5/14532* (2013.01); *A61B 5/1455* (2013.01); *A61B 5/1495* (2013.01); *A61B 5/14546* (2013.01); *A61B 5/7267* (2013.01); *A61B 5/7275* (2013.01); *G01N 33/4833* (2013.01); *G16H 50/20* (2018.01); *A61B 2560/0223* (2013.01); *G01N 21/35* (2013.01); *G01N 2201/129* (2013.01)

(58) Field of Classification Search
None
See application file for complete search history.

(56) References Cited

U.S. PATENT DOCUMENTS

| | | | |
|---|---|---|---|
| 6,528,809 B1 | 3/2003 | Thomas et al. | |
| 6,645,142 B2 | 11/2003 | Braig et al. | |
| 7,098,037 B2 | 8/2006 | Haas et al. | |
| 7,460,895 B2 | 12/2008 | Arnold et al. | |
| 7,591,801 B2 | 9/2009 | Brauker et al. | |
| 2003/0023152 A1 | 1/2003 | Abbink et al. | |
| 2003/0050541 A1 | 3/2003 | Wuori | |
| 2006/0167348 A1 | 7/2006 | Arnold et al. | |
| 2009/0098587 A1 | 4/2009 | Hetzel et al. | |
| 2011/0225112 A1* | 9/2011 | Cameron | G06F 19/3456 706/20 |
| 2014/0316228 A1 | 10/2014 | Blank et al. | |
| 2016/0283241 A1 | 9/2016 | Stuttard et al. | |

FOREIGN PATENT DOCUMENTS

| | | |
|---|---|---|
| CN | 1620263 | 5/2005 |
| JP | 2003524761 | 8/2003 |
| JP | 2004514494 | 5/2004 |
| JP | 2004321325 | 11/2004 |
| JP | 2007525276 | 9/2007 |
| JP | 2008005920 | 1/2008 |
| JP | 2010005047 | 1/2010 |
| WO | 02065090 | 8/2002 |

OTHER PUBLICATIONS

McShane, Michael J., et al. "A novel peak-hopping stepwise feature selection method with application to Raman spectroscopy1." Analytica chimica acta 388.3 (1999): 251-264.*
Extended European Search Report—European Patent Application No. 16189720.2 dated Mar. 2, 2017, citing references listed within.
Chinese Office Action—Chinese Patent Application No. 201610848249.7 dated Apr. 2, 2020, citing references listed within.
Japanese Office Action-Japanese Patent Application No. 2016-179957 dated Jun. 23, 2020, citing references listed within.

* cited by examiner

*Primary Examiner* — G Steven Vanni
(74) *Attorney, Agent, or Firm* — Cantor Colburn LLP

(57) ABSTRACT

A method for predicting a concentration of an in vivo analyte includes obtaining a plurality of in vivo spectra of the in vivo analyte, determining a learning section for a concentration predicting algorithm for the analyte based on an unchanged section, during which the concentration of the analyte is not substantially changed, and a plurality of the in vivo spectra, and predicting the concentration of the in vivo analyte by using the concentration predicting algorithm based on a learned result of the learning section and an intrinsic spectrum of the in vivo analyte.

27 Claims, 17 Drawing Sheets

Alignment of baselines

METHOD AND APPARATUS FOR PREDICTING IN VIVO ANALYTE CONCENTRATION USING LEARNING AND A NET ANALYTE SIGNAL

CROSS-REFERENCE TO RELATED APPLICATION

This application claims priority to Korean Patent Application No. 10-2015-0134872, filed on Sep. 23, 2015, and all the benefits accruing therefrom under 35 U.S.C. § 119, the content of which in its entirety is herein incorporated by reference.

BACKGROUND (a) Field

Exemplary embodiments of the invention relate to a method and an apparatus for predicting a concentration of an in vivo analyte from a biological signal.

(b) Description of the Related Art

For predicting a concentration of in vivo analyte from a biological signal, a partial least squares ("PLS") algorithm or a net analyte signal ("NAS") algorithm may be employed. Further, after projecting an electromagnetic wave such as an infrared ray or the like to a test subject, an in vivo spectrum obtained by a result of an interaction between an analyte and the electromagnetic wave may be used in the above-stated algorithms for predicting the concentration of the in vivo analyte. Herein, the in vivo spectrum may be obtained by using an optical method such as infra-red spectroscopy, a Raman spectroscopy, or the like.

The PLS algorithm is a statistical modeling tool for obtaining a correlation between a multivariate input variable (independent variable) and an output variable (dependent variable) by using data obtained from an experiment or the like. The PLS algorithm is applied to analyzation of the biological signal, an analyte concentration at a certain time may be predicted from the biological signal by learning a spectral change depending on the analyte concentration. The PLS algorithm uses the analyte concentration at a plurality of times and spectra obtained at corresponding times thereof to predict the analyte concentration from the biological signal, and it is desired to periodically relearn the spectral change depending on a change of the analyte concentration to prevent deterioration of predictability.

The NAS algorithm predicts the analyte concentration by learning an intrinsic spectrum of the analyte and a spectrum changing factor irrelevant to the analyte concentration. When the NAS algorithm is applied to the analyzation of the biological signal, the analyte concentration at other times may be predicted from a spectrum at a specific time and the intrinsic spectrum of the analyte obtained from the experiment by learning the spectrum changing factor except for the change of the analyte concentration in a time section, during which the concentration of the analyte is constantly maintained. In other words, the NAS algorithm learns that the spectral change in the time section (learning section), during which the concentration of the analyte is not changed, is irrelevant to the change of the analyte concentration, and then predicts the analyte concentration in the time section (predicting section), which is other than the learning section, by using this learned information and the intrinsic spectrum of the analyte.

The above information disclosed in this Background section is only for enhancement of understanding of the background of the invention and therefore it may contain information that does not form the prior art that is already known in this country to a person of ordinary skill in the art.

SUMMARY

In a net analyte signal ("NAS") algorithm, a prediction accuracy of the analyte concentration is improved in the case that changing factors of the biological signal in the learning section and in the predicting section are identical to each other. However, the prediction accuracy of the concentration is deteriorated if the changing factor of the biological signal that is not generated in the predicting section is additionally learned in the learning section, i.e., unnecessary learning occurs. Further, in the case that an unlearned changing factor of the biological signal is generated in the predicting section, the prediction accuracy is also deteriorated. Therefore, it is very important to control such an extraneous factor in order to improve the prediction accuracy of the concentration. Conventionally, several techniques for improving the prediction accuracy of the NAS algorithm have been suggested. However, any method capable of controlling the extraneous factor effectively has not been researched.

Exemplary embodiments of the invention relate to a method and an apparatus for predicting an analyte concentration employing categorizing a section of in vivo spectra as a similar section by calculating a similarity between the spectra and determining a learning section using a section during which the in vivo analyte concentration is relatively constantly maintained in each similar section, and then predicting the in vivo analyte concentration in the similar section including the learning section by using the learning section thereof, in an algorithm, such as the NAS algorithm and the like, for predicting the in vivo analyte concentration by learning a change of the spectrum in the section during which the in vivo analyte concentration is relatively constantly maintained.

According to an exemplary embodiment of the invention, a method for predicting a concentration of an in vivo analyte includes obtaining a plurality of in vivo spectra of the in vivo analyte; determining a learning section of a concentration predicting algorithm for the in vivo analyte based on an unchanged section, during which a concentration of the in vivo analyte is not substantially changed, and the in vivo spectra; and predicting the concentration of the in vivo analyte by using the concentration predicting algorithm based on a learned result of the learning section and an intrinsic spectrum of the in vivo analyte.

In an exemplary embodiment, the in vivo analyte may be at least one of glucose, urea, lactate, triglyceride, protein, cholesterol, and ethanol.

In an exemplary embodiment, the in vivo analyte may be glucose and the unchanged section, during which the concentration of the in vivo analyte is not substantially changed, may be a fasting section.

In an exemplary embodiment, the in vivo spectrum may include at least one of an absorption spectrum and a reflection spectrum of an infra-red ray.

In an exemplary embodiment, the in vivo spectrum may include a dispersion spectrum of a single wavelength electromagnetic wave.

In an exemplary embodiment, the obtaining the in vivo spectra of the in vivo analyte may include obtaining the in vivo spectra continually at a predetermined time interval.

In an exemplary embodiment, the concentration predicting algorithm may include a NAS algorithm.

In an exemplary embodiment, the determining the learning section may include calculating a similarity between the in vivo spectra, determining a section having a high similarity as the similar section, and determining a section, during which the unchanged section and the similar section overlap each other, as the learning section.

In an exemplary embodiment, the calculating the similarity between the in vivo spectra comprises may include aligning baselines of at least two spectra for calculating similarities thereof among the in vivo spectra, and calculating a difference between the at least two in vivo spectra, the baselines of which are aligned.

In an exemplary embodiment, the predicting the concentration of the in vivo analyte may include predicting the concentration of the in vivo analyte in the similar section including the learning section when a length of the learning section is longer than a predetermined section length.

In an exemplary embodiment, the predicting the concentration of the in vivo analyte may include re-determining the learning section in the similar section when the length of the learning section is shorter than a predetermined length.

In an exemplary embodiment, the predicting the concentration of the in vivo analyte may include displaying a message to inform a user that a concentration prediction is unavailable when a length of the learning section is shorter than a predetermined length.

In an exemplary embodiment, the in vivo analyte may be included in a human body, an animal, a mammal, a non-mammal, or a microorganism.

According to another exemplary embodiment of the invention, an apparatus for predicting a concentration of an in vivo analyte, includes: a processor; and a memory, where the processor executes a program stored in the memory to: obtaining a plurality of in vivo spectra of the in vivo analyte; determining a learning section of a concentration predicting algorithm for the in vivo analyte based on an unchanged section, during which a concentration of the in vivo analyte is not substantially changed, and the in vivo spectra; and predicting the concentration of the in vivo analyte by using the concentration predicting algorithm based on the learned result of the learning section and an intrinsic spectrum of the in vivo analyte.

In an exemplary embodiment, the in vivo analyte may be at least one of glucose, urea, lactate, triglyceride, protein, cholesterol, and ethanol.

In an exemplary embodiment, the in vivo analyte may be glucose, and the unchanged section, during which the concentration of the in vivo analyte is not substantially changed, may be a fasting section.

In an exemplary embodiment, the in vivo spectrum may include at least one of an absorption spectrum and a reflection spectrum of an infra-red ray.

In an exemplary embodiment, the in vivo spectrum may include a dispersion spectrum of a single wavelength electromagnetic wave.

In an exemplary embodiment, when the processor performs the obtaining the in vivo spectra of the in vivo analyte, the processor may perform obtaining the in vivo spectra continually at the predetermined time interval.

In an exemplary embodiment, the concentration predicting algorithm may include a NAS algorithm.

In an exemplary embodiment, when the processor performs the determining the learning section, the processor may perform: calculating a similarity between the in vivo spectra, determining a section having a high similarity as the similar section; and determining a section, during which the unchanged section and the similar section overlap each other, as the learning section.

In an exemplary embodiment, when the processor performs the calculating of the similarity, the at least one processor may perform steps including aligning baselines of at least two spectra for calculating similarities thereof among the in vivo spectra, and calculating the difference between the at least two in vivo spectra whose baselines are aligned.

In an exemplary embodiment, when the processor performs the predicting the concentration of the in vivo analyte, the processor may perform predicting the concentration of the in vivo analyte in the similar section including the learning section, in a case that a length of the learning section is longer than a predetermined section length.

In an exemplary embodiment, when the processor performs the predicting the concentration of the in vivo analyte, processor may perform re-determining the learning section in the similar section, in a case that a length of the learning section is shorter than a predetermined length.

In an exemplary embodiment, when the processor performs the predicting the concentration of the in vivo analyte, the processor performs displaying a message to inform a user that the concentration prediction is unavailable, in a case that a length of the learning section is shorter than a predetermined length.

In an exemplary embodiment, the in vivo analyte may be included in a human body, an animal, a mammal, a non-mammal, or a microorganism.

In an exemplary embodiment, the apparatus for predicting the analyte concentration may further include a communicator which receives the in vivo spectra from an infra-red sensor or a laser sensor through a wired or wireless network.

In an exemplary embodiment, the apparatus for predicting the analyte concentration may further include an infra-red sensor which generates the in vivo spectra by radiating infra-red rays to a human body.

In an exemplary embodiment, the apparatus for predicting the in vivo analyte concentration may further include a laser sensor which generates the in vivo spectra by radiating a laser to a human body.

According to exemplary embodiments of the invention, the in vivo analyte concentration may be predicted precisely by predicting the in vivo analyte concentration in the similar section, while using the determining of the section that no extraneous factor occurs as the similar section of a biological signal by determining an occurring point of the extraneous factor such as the change of a measuring position or the like through calculating the similarity between the biological signals, and determining the section maintaining the in vivo analyte concentration at the constant in each similar section as the learning section.

BRIEF DESCRIPTION OF THE DRAWINGS

These and/or other features of the invention will become apparent and more readily appreciated from the following detailed description of embodiments thereof, taken in conjunction with the accompanying drawings, in which.

DETAILED DESCRIPTION

Figure 1:
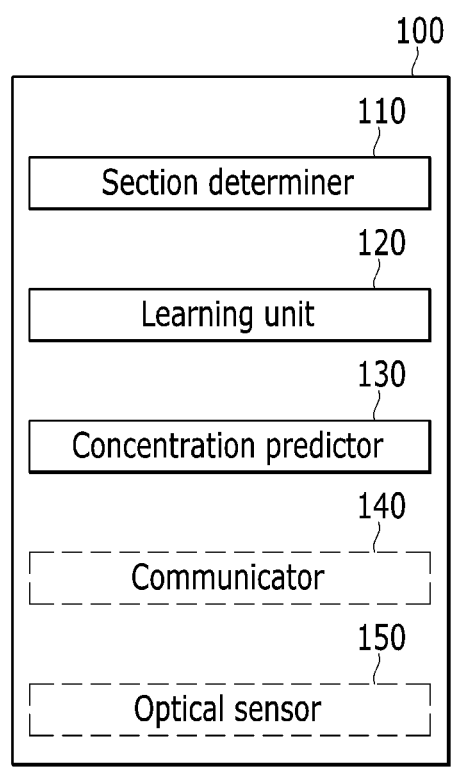
FIG. 1 is a block diagram illustrating an exemplary embodiment of a concentration predicting apparatus for predicting a concentration of an analyte, according to the invention.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 is a block diagram illustrating an exemplary embodiment of a concentration predicting apparatus for predicting a concentration of an analyte, e.g., an in vivo analyte, according to the invention.

In an exemplary embodiment, the concentration predicting apparatus 100 may be configured to predict the concentration of the analyte by analyzing an in vivo spectrum thereof using a concentration predicting algorithm for the analyte. Herein, the in vivo spectrum may be generated when infer-red rays or laser beams (that is, single wavelength electromagnetic waves) are transmitted or diffusely reflected to an organism, e.g., a human body, and then absorbed or dispersed by the analyte therein, and may be obtained continually at a predetermined time interval. That is, the in vivo spectrum may include the absorption spectrum and the reflection spectrum of the infra-red ray, or may include the dispersion spectrum of the single wavelength electromagnetic waves. The in vivo spectrum may be applied to the concentration predicting algorithm after being obtained by an infra-red spectroscopy or a Raman spectroscopy. The in vivo spectrum may be one of an absorption spectrum and a reflection spectrum of an infra-red ray or a dispersion spectrum of a single wavelength electromagnetic wave. In such an embodiment, the concentration predicting apparatus 100 may predict the concentration of an in vivo analyte of a human body, an animal, a mammal, non-mammal, or a microorganism. In such an embodiment, the in vivo analyte may be at least one of glucose, urea, lactate, triglyceride, protein, cholesterol and ethanol.

In such an embodiment, where the in vivo analyte is glucose, the concentration of the analyte may represent a blood sugar level, and a time section during which an analyte concentration is substantially constantly maintained, may represent a fasting section. In such an embodiment, where the in vivo analyte is glucose, near infra-red ("NIR")

or middle infra-red ("MIR") rays may be used for generating the in vivo spectrum of glucose.

Referring to FIG. 1, an exemplary embodiment of the concentration predicting apparatus 100 includes a section determiner 110, a learning unit 120, and a concentration predictor 130.

In an exemplary embodiment, the section determiner 110 may be configured to categorize sections of a plurality of in vivo spectra, each obtained continually at a predetermined time interval, which may be about a one-minute time interval, as similar sections based on calculated similarity between the plurality of in vivo spectra, and determine a learning section in each similar section based on a section during which the analyte concentration is substantially constantly maintained (for example, a section during which no analyte such as glucose or the like is introduced into the human body, like the fasting section). In such an embodiment, when a length of the learning section is shorter than that of a predetermined section, e.g., a time duration of about 20 minutes to about 30 minutes, the section determiner 110 may determine that a concentration prediction is unavailable based on the learning section and display a message to inform a user that the concentration prediction is unavailable through an interface or a display device (not shown) or the like in the concentration predicting apparatus 100.

In an exemplary embodiment, the learning unit 120 is configured to learn a spectrum changing factor irrelevant to a change of the analyte concentration based on an in vivo spectrum in each learning section that is determined by the section determiner 110. In such an embodiment, the learning unit 120 may learn the spectrum changing factor irrelevant to the change of the analyte concentration by employing a principal component analysis ("PCA") method or the like.

In an exemplary embodiment, the concentration predictor 130 is configured to predict the analyte concentration by using an intrinsic spectrum of the analyte and a learned result of the learning section, e.g., the spectrum changing factor in each learning section. In such an embodiment, the concentration predictor 130 may predict an in vivo concentration of the analyte by using a least square method. Then, the concentration predictor 130 may deliver a predicted result of the analyte through a communicator 140, or display the predicted result of the concentration to the user through the interface or the like, e.g., a display device, in the concentration predicting apparatus 100.

In an exemplary embodiment, a net analyte signal ("NAS") algorithm may be used for predicting the analyte concentration, e.g., the blood sugar level, and the concentration predicting apparatus may predict the blood sugar level in the section that is other than the learning section (e.g., the predicting section in the similar section) by learning that the change of the in vivo spectrum in the fasting section is irrelevant to the change of the blood sugar level and by analyzing the change of the in vivo spectrum. In a conventional concentration predicting apparatus, an entire fasting section is determined as the learning section, such that a changing factor in the fasting section that changes the in vivo spectrum in the fasting section irrelevant to the change of the blood sugar level such as the change of a position, at which the in vivo spectrum is obtained in the fasting section, may influence a prediction of the blood sugar level, thereby deteriorating the prediction accuracy of the concentration. An exemplary embodiment of the concentration predicting apparatus according to the invention may improve the prediction accuracy of the concentration by accurately restricting the learning section and the predicting section (the section that is other than the learning section in the similar section) by determining when the extraneous factor that causes a change, such as the change of a position, at which the in vivo spectrum is obtained in the fasting section, occurs based on the similarity between the in vivo spectra.

In an exemplary embodiment, where the in vivo spectrum is generated by an optical sensor disposed in an exterior of the concentration predicting apparatus, the concentration predicting apparatus 100 may further include the communicator 140 configured to obtain the in vivo spectrum from the optical sensor through a wired or wireless network. In such an embodiment, the communicator 140 may be configured to transmit the predicted result of the analyte concentration to the outside of the concentration predicting apparatus 100 through the wired or wireless communication.

Alternatively, the concentration predicting apparatus 100 may further include an optical sensor 150 to obtain the in vivo spectrum.

In an exemplary embodiment, the concentration predicting apparatus may be operated by a processor, a memory, and a transceiver. The memory may be connected to the processor to store diverse information for operating the processor. The transceiver may be connected to the processor to transmit and receive wired or wireless signals to and from a terminal, a server, or the like. The processor may be configured to implement a function, a process, or a method according to an exemplary embodiment of the invention. An operation of an exemplary embodiment of the concentration predicting apparatus according to the invention may be implemented by the processor.

In an exemplary embodiment of the invention, the memory may be disposed in an interior or exterior of the processor, and may be connected to the processor by various already known means. The memory may be one of various volatile and non-volatile storing media. In one exemplary embodiment, for example, the memory may include a read-only memory ("ROM") or a random access memory ("RAM").

Figure 2:
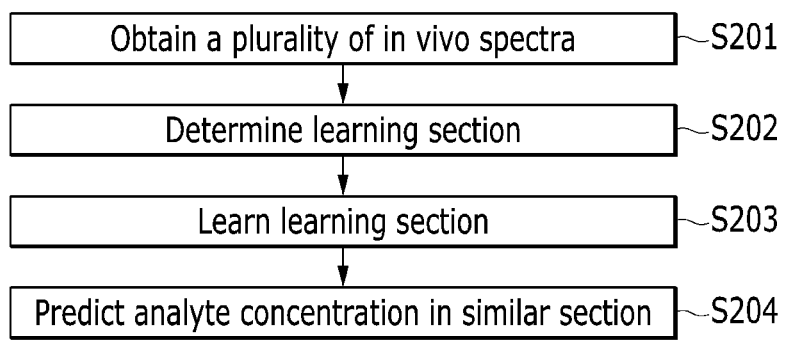
FIG. 2 is a flowchart illustrating an exemplary embodiment of a method for predicting a blood sugar level, according to the invention.

FIG. 2 is a flowchart illustrating an exemplary embodiment of a method for predicting a blood sugar level, according to the invention.

Referring to FIG. 2, in an exemplary embodiment, a plurality of the in vivo spectra of the analyte in the human body is obtained continually (S201). In such an embodiment, a plurality of the in vivo spectra may be obtained continually at the predetermined time interval, e.g., a one-minute interval.

In such an embodiment, the section determiner 110 determines a learning section for a concentration predicting algorithm based on a similarity between the spectra and a section during which an analyte concentration is relatively constantly maintained (S202). In such an embodiment, the section determiner 110 may effectively control the extraneous factor that may affect the concentration prediction of the analyte, since the occurrence of the extraneous factor may be determined based on the similarity of the in vivo spectra.

Figure 3A:
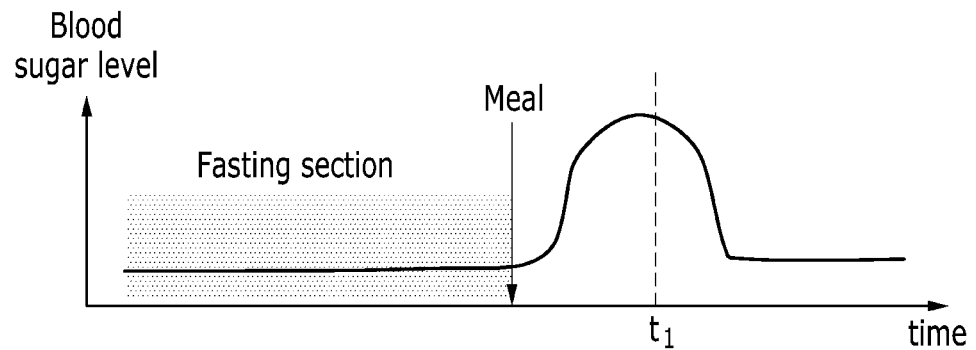
FIG. 3A and FIG. 3B are drawings illustrating an extraneous factor that may be generated in a fasting section according to an exemplary embodiment of the invention.
Figure 3B:
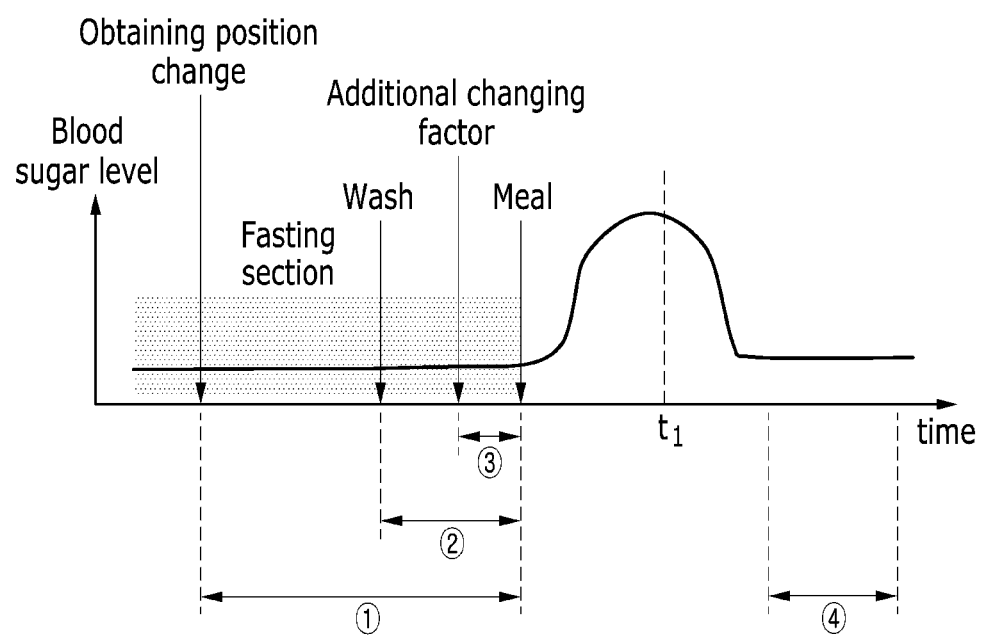

FIG. 3A and FIG. 3B illustrate the extraneous factor that may be generated in the fasting section according to an exemplary embodiment of the invention.

FIG. 3A and FIG. 3B are graphs in which a horizontal axis indicates a time and a vertical axis indicates the blood sugar level, and a solid line thereof shows the change of the blood sugar level depending on the time. FIG. 3A and FIG. 3B are graphs illustrating a case that the analyte is glucose and the analyte concentration is the blood sugar level.

Referring to FIG. 3A, the blood sugar level of a user of an exemplary embodiment of the concentration predicting apparatus is increased after a meal time, and the time section or an unchanged section, during which the analyte concentration is not substantially changed, e.g., the fasting section, may be determined as a time section before meal time.

In such an embodiment, a significant change of the in vivo spectrum may occur in the fasting section by the changing factor, such as the change of the obtaining position of the in vivo spectrum, a skin wash or the like. In such an embodiment, the length of the learning section may be changed depending on an occurrence of the changing factor in the fasting section.

Referring to FIG. 3B, in such an embodiment, when a measuring position of the in vivo spectrum is changed, the learning section is changed to a shorter section (section ①) than the fasting section, and when the measuring position of the in vivo spectrum is changed due to the skin wash thereafter, the learning section may be changed to an even shorter section (section ②). In such an embodiment, if the learning section is changed to an insufficiently short section (section ③) after the occurrence of the changing factor in the fasting section is too close to the meal time, the prediction of the blood sugar level may be failed because of an insufficiency of the learning section. In such an embodiment, when the length of the learning section is shorter than the predetermined section length, e.g., a time duration of about 20 minutes to about 30 minutes, the concentration prediction of the analyte in the similar section including the learning section may be determined to be unavailable. In such an embodiment, the concentration predictor 130 may predict the analyte concentration in the similar section including the learning section, when the length of the learning section is longer than that of a predetermined section. In such an embodiment, the section determiner 110 may inform the user that the concentration prediction is unavailable through an interface or the display device of the concentration predicting apparatus, since the length of the learning section is shorter than that of the predetermined section. If the learning section (section ④) in the similar section may be additionally determined by the analysis on the similarity between the spectra even after the meal time, the prediction of the blood sugar level in the similar section may be available. In an exemplary embodiment, as described above, since the extraneous factor such as the change of the measuring position of the in vivo spectrum, the skin wash or the like may affect the prediction of the blood sugar level, the section determiner 110 may remove the extraneous factor by determining a similar section, which is a continuous section having no extraneous factor, based on the similarity between the spectra.

Figure 4:
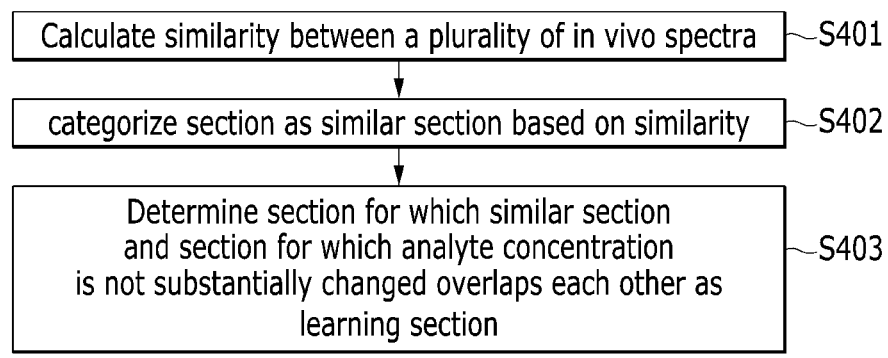
FIG. 4 is a flowchart illustrating an exemplary embodiment of a method for determining a learning section of a predicting algorithm for the blood sugar level, according to the invention.
Figure 5:
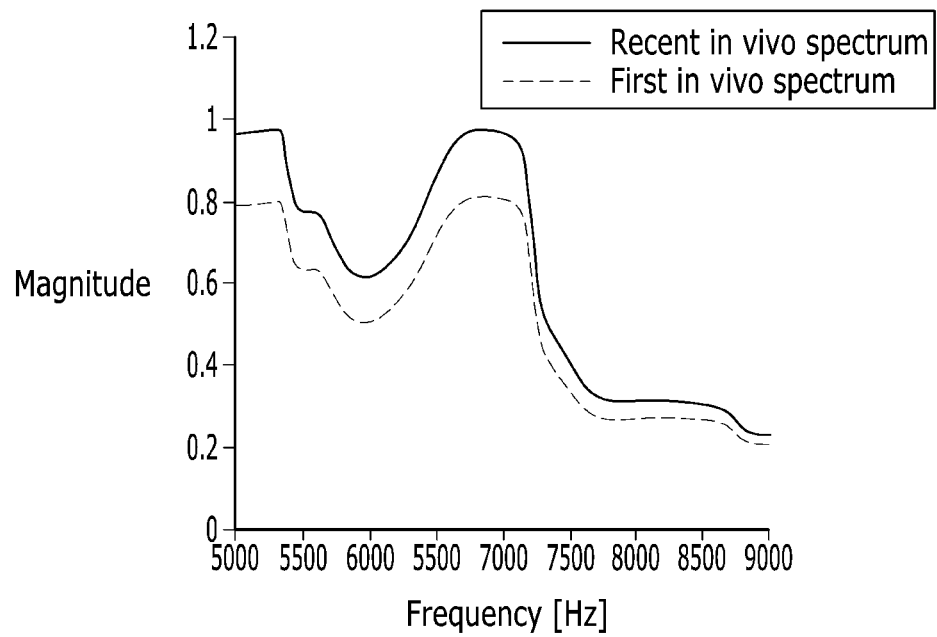
FIG. 5 is a graph illustrating an exemplary embodiment of a method for a similarity analysis between in vivo spectra, according to the invention.
Figure 5:
Figure 5:
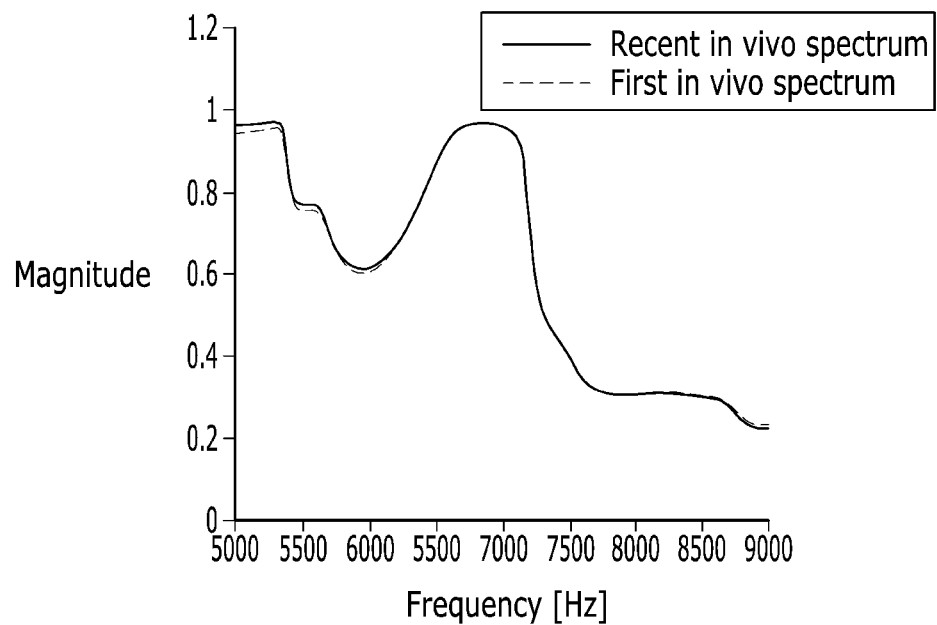
Figure 6:
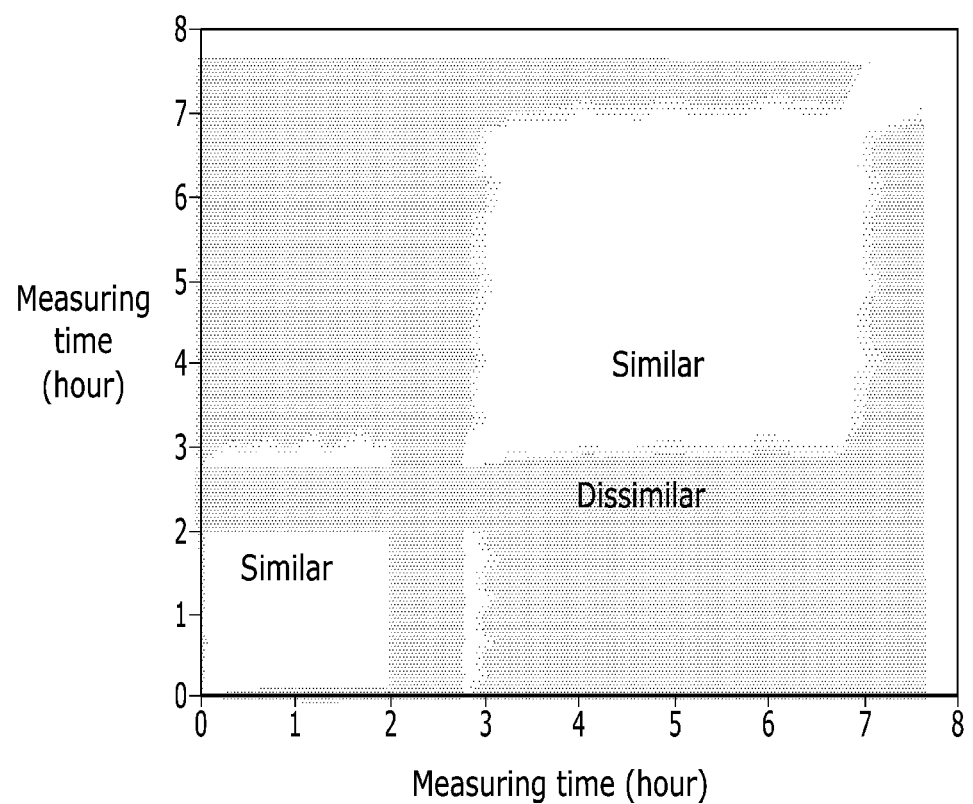
FIG. 6 is a graph illustrating a calculated similarity between in vivo spectra according to an exemplary embodiment of the invention.

FIG. 4 is a flowchart illustrating to an exemplary embodiment of a method for determining a learning section of a predicting algorithm for the blood sugar level, according the invention, FIG. 5 is a graph illustrating an exemplary embodiment of a method for a similarity analysis between in vivo spectra, according to the invention, and FIG. 6 is a graph illustrating a calculated similarity between in vivo spectra according to an exemplary embodiment of the invention.

In an exemplary embodiment, the section determiner 110 of the concentration predicting apparatus calculates a similarity between in vivo spectra to remove an extraneous factor such as a change of a measuring position or the like from the prediction of the blood sugar level (S401). In such an embodiment, the section determiner 110 categorizes sections of the in vivo spectra as similar sections based on the calculated similarity (S402). In such an embodiment, the section determiner 110 may find an occurrence or occurring time of the extraneous factor by categorizing the sections of the in vivo spectra as similar sections. In such an embodiment, the sections of the in vivo spectrum may be categorized as the similar sections based on the occurring time of the extraneous factor. In such an embodiment, the section determiner 110 determines an unchanged section during which the analyte concentration is not substantially changed in each similar section as the learning section (S403). In such an embodiment, the learning section may be determined as a section, during which the similar section and the unchanged section (e.g., the fasting section) overlap each other.

In an exemplary embodiment of the invention, a similarity between the in vivo spectra may be calculated by a one-to-one comparison between the in vivo spectra obtained continually.

FIG. 5 to FIG. 11 are graphs illustrating a predicted result of the blood sugar level of a rat. In the prediction of the blood sugar level according to the exemplary embodiment of the invention, the blood sugar level is changed by injecting a high concentration glucose solution into an artery of the rat and an infra-red spectrum of a skin thereof is measured at a time interval of about 1.2 minutes.

The horizontal axis of upper and lower graphs of FIG. 5 represents a frequency of the in vivo spectrum and the vertical axis thereof represents a magnitude of the in vivo spectrum. Referring to FIG. 5, the upper graph illustrates two infra-red spectra measured at different times, and the lower graph illustrates the spectra whose baselines are aligned for a similarity calculation. In an exemplary embodiment of the invention, as shown in FIG. 5, the similarity may be calculated based on a difference between two in vivo spectra after the baselines of the in vivo spectra are aligned for the similarity calculation. In an alternative exemplary embodiment of the invention, another method for calculating the spectral change caused by the extraneous factor, for example, calculating the difference between spectra without the baseline fitting, comparing the Fourier transforms result, and determining the extraneous factor by using changes of a specific spectrum (e.g., a frequency of about 4200 $cm^{-1}$), may be employed.

Referring to FIG. 6, the horizontal axis and the vertical axis respectively represent measuring times of two spectra for calculating the similarity among continually measured spectra, and the calculated similarity is illustrated by a shade. As shown in FIG. 6, an in vivo spectrum measured at about 1 hour may be similar to an in vivo spectrum measured between about zero (0) hour and about 2 hours, but may be dissimilar to an in vivo spectrum measured between about 2 hours and about 7 hours. As shown in FIG. 6, an in vivo spectrum measured at about 5 hours may be dissimilar to an in vivo spectrum measured between about zero (0) hour and about 3 hours, but may be similar to an in vivo spectrum measured between about 3 hours and about 7 hours.

Figure 7A:
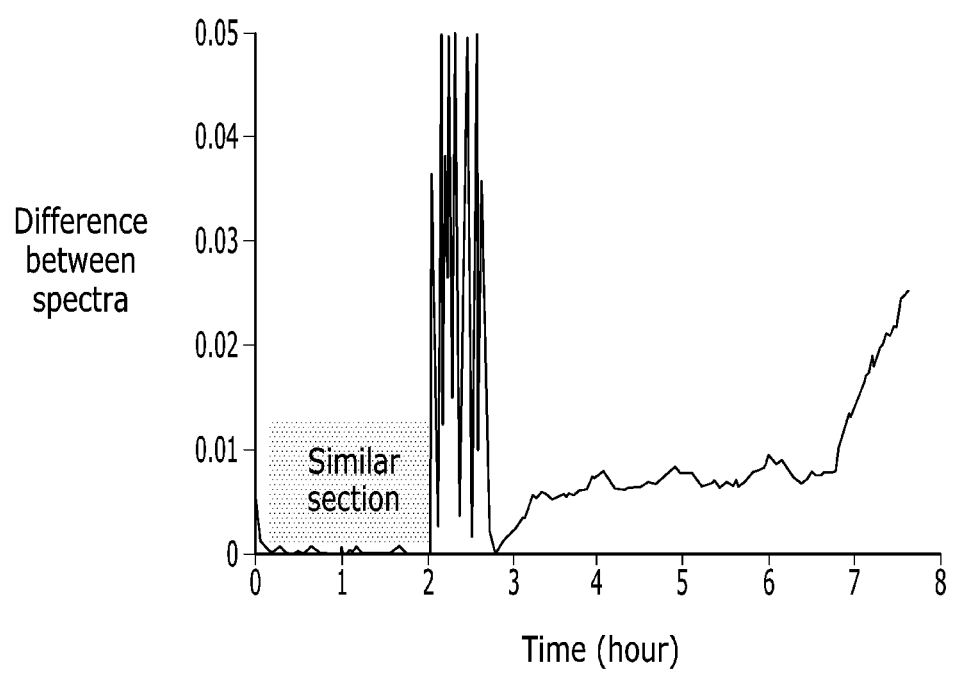
FIG. 7A and FIG. 7B illustrate a similar section determined based on a similarity between in vivo spectra according to an exemplary embodiment of the invention.
Figure 7B:
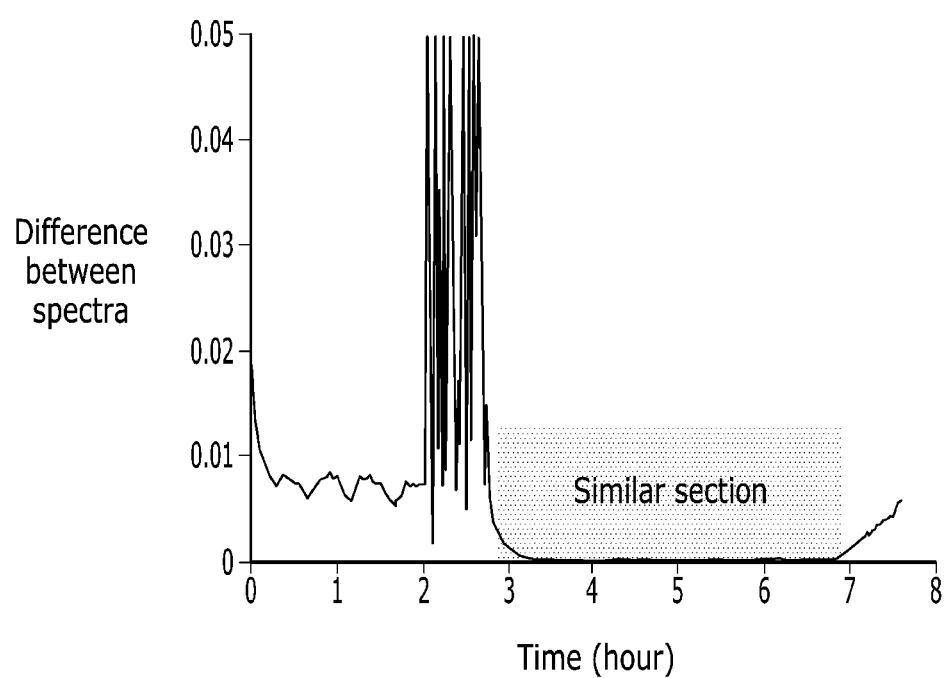

In such an embodiment, the section determiner 110 of the concentration predicting apparatus determines the similar sections based on the calculated similarity. FIG. 7A and FIG. 7B illustrate similar sections determined based on the similarity between in vivo spectra shown in FIG. 6 according to an exemplary embodiment of the invention.

FIG. 7A is a graph illustrating a difference between an in vivo spectrum measured at about 1 hour and an in vivo spectrum measured at a different time, and FIG. 7B is a graph illustrating a difference between an in vivo spectrum measured at about 5 hours and an in vivo spectrum measured at a different time. In FIG. 7A and FIG. 7B, the horizontal axis represents a measuring time of the in vivo spectrum, the vertical axis of FIG. 7A represents the difference between the in vivo spectrum measured at about 1 hour and the in vivo spectrum measured at the different time, and the vertical axis of FIG. 7B represents the difference between the in vivo spectrum measured at about 5 hours and the in vivo spectrum measured at the different time.

Referring to FIG. 7A, since the in vivo spectrum measured at about 1 hour is similar to an in vivo spectrum measured between about 20 minutes and about 2 hours, a section from about 20 minutes to about 2 hours may be determined as the similar section. Referring to FIG. 7B, since the in vivo spectrum measured at about 5 hours is similar to an in vivo spectrum measured between about 3 hours 20 minutes and about 6 hours 55 minutes, a section from about 3 hours 20 minutes to about 6 hours 55 minutes may be determined as a similar section having a high similarity between the in vivo spectra. Herein, the similarity may be changed depending on a predetermined threshold when the similar section is determined. Further, the biological signal such as a temperature, a pressure, an impedance of the skin, or the like may be used additionally when the similar section is determined.

In such an embodiment, the section determiner 110 may determine a section, during which the similar section and the unchanged section overlap each other, as the learning section.

Figure 8:
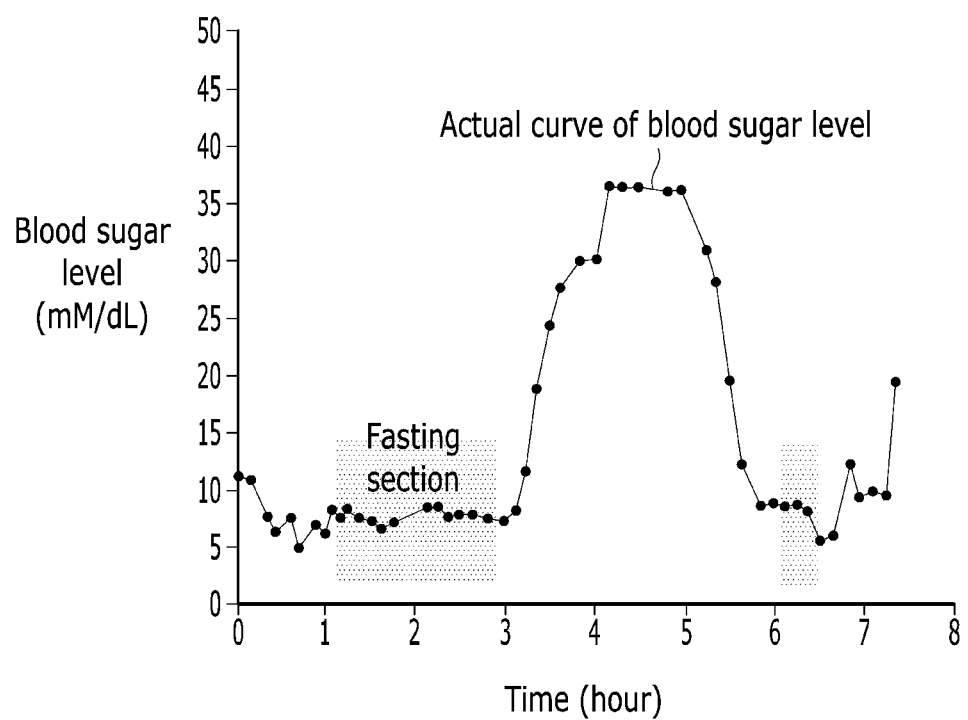
FIG. 8 is a graph illustrating a fasting section according to an exemplary embodiment of the invention.
Figure 9:
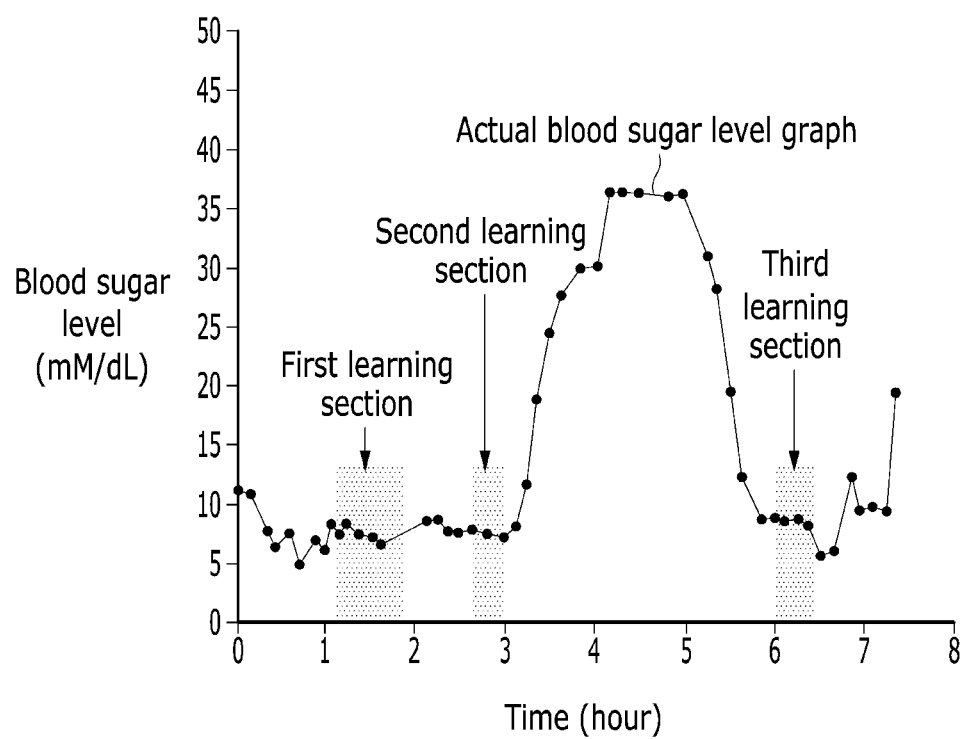
FIG. 9 is a graph illustrating the learning section determined according to an exemplary embodiment of the invention.

FIG. 8 is a graph illustrating a fasting section according to an exemplary embodiment of the invention, and FIG. 9 is a graph illustrating a learning section determined according to an exemplary embodiment of the invention.

Referring to FIG. 8, a solid line therein indicates curves illustrating the change of the blood sugar level with respect to time, and the unchanged section, during which the blood sugar level (i.e., the in vivo concentration of glucose) is not substantially changed, may be determined as the fasting section in FIG. 8. The fasting section illustrated in FIG. 8 includes sections from about 1 hour to about 3 hours and from about 6 hours to about 6.5 hours. In an exemplary embodiment, the fasting section may be determined as an interval during (e.g., throughout) which the actual blood sugar level is maintained substantially constant when the actual blood sugar level is sensed every 10 minute interval. In an alternative exemplary embodiment, a user of the concentration predicting apparatus may input the fasting section, which may be measured manually by the user or predetermined according to a life cycle of the user, into the concentration predicting apparatus. In an exemplary embodiment, for example, the fasting section may be determined based on an eating time. In such an embodiment, where the eating time is used for determining the fasting section, an interval from a time point after a predetermined time from a first eating time point to a second eating time point may be determined as the fasting section. In such an embodiment, in a case where a user has a breakfast at 8 AM and a lunch at 1 PM, and the predetermined time is 3 hours, the fasting section is for 2 hours from 11 AM to 1 PM.

Further, referring to FIG. 9, the learning section, during which the unchanged section, during which the analyte concentration is not substantially changed, and the similar section, during which the in vivo spectra are similar to each other, overlap each other, includes sections from about 1 hour to about 2 hours (a first learning section), from about 2.5 hours to about 3 hours (a second learning section), and from about 6 hours to about 6.5 hours (a third learning section).

In such an embodiment, the learning section may be applied to another algorithm for predicting the analyte concentration by learning that the change of the in vivo spectrum in the unchanged section, during which the analyte concentration is not substantially changed, is irrelevant to the analyte, in addition to the NAS algorithm.

Referring back to FIG. 1 and FIG. 2, in an exemplary embodiment, the learning unit 120 learns each learning section (S203). In one exemplary embodiment, for example, the learning unit 120 may learn the spectrum changing factor irrelevant to the change of the analyte concentration based on the in vivo spectrum in each learning section. In an exemplary embodiment, the concentration predictor 130 predicts the analyte concentration in the similar section based on learned results of the learning sections and the intrinsic spectrum of the analyte (S204).

Figure 10:
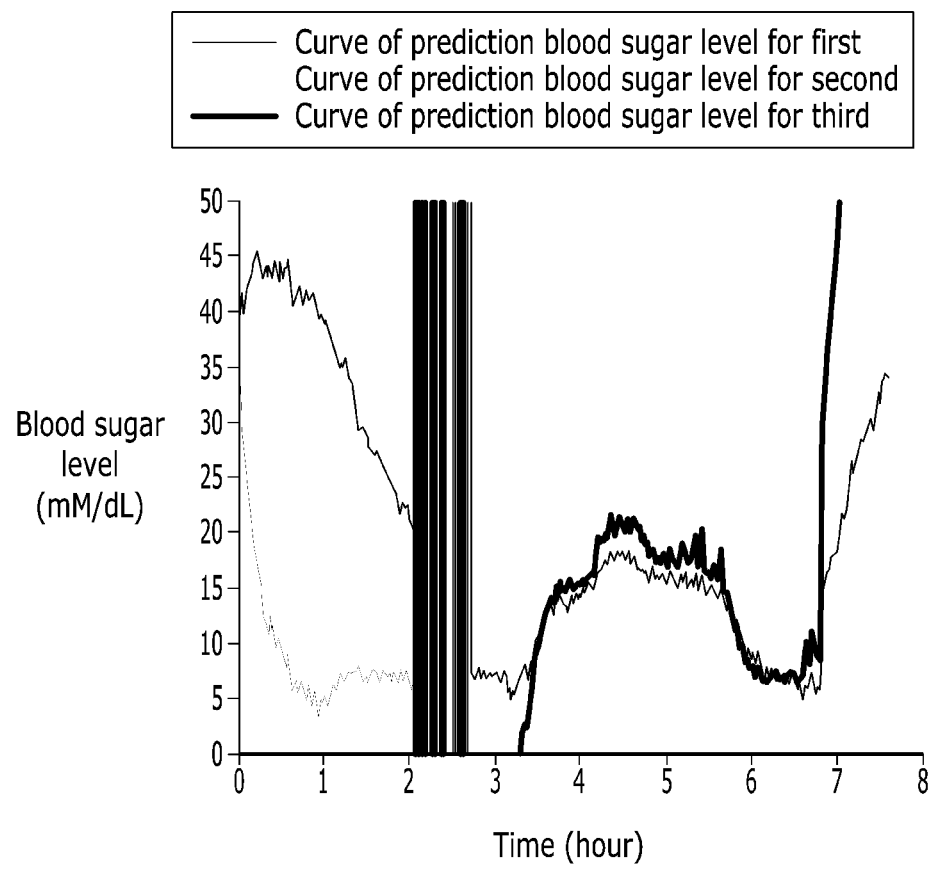
FIG. 10 is a graph illustrating a result obtained by performing an exemplary embodiment of a concentration predicting algorithm according to the invention.

FIG. 10 is a graph illustrating a result obtained by performing a concentration predicting algorithm according to an exemplary embodiment of the invention.

Referring to FIG. 10, three curves illustrating performed results of the concentration predicting algorithm related to each learning section (the first, second, and third learning sections) are shown. Since each curve illustrated in FIG. 10 is valid only in the similar section including a corresponding learning section, a final predicted result may be acquired by combining the curves based on the similar section.

Figure 11A:
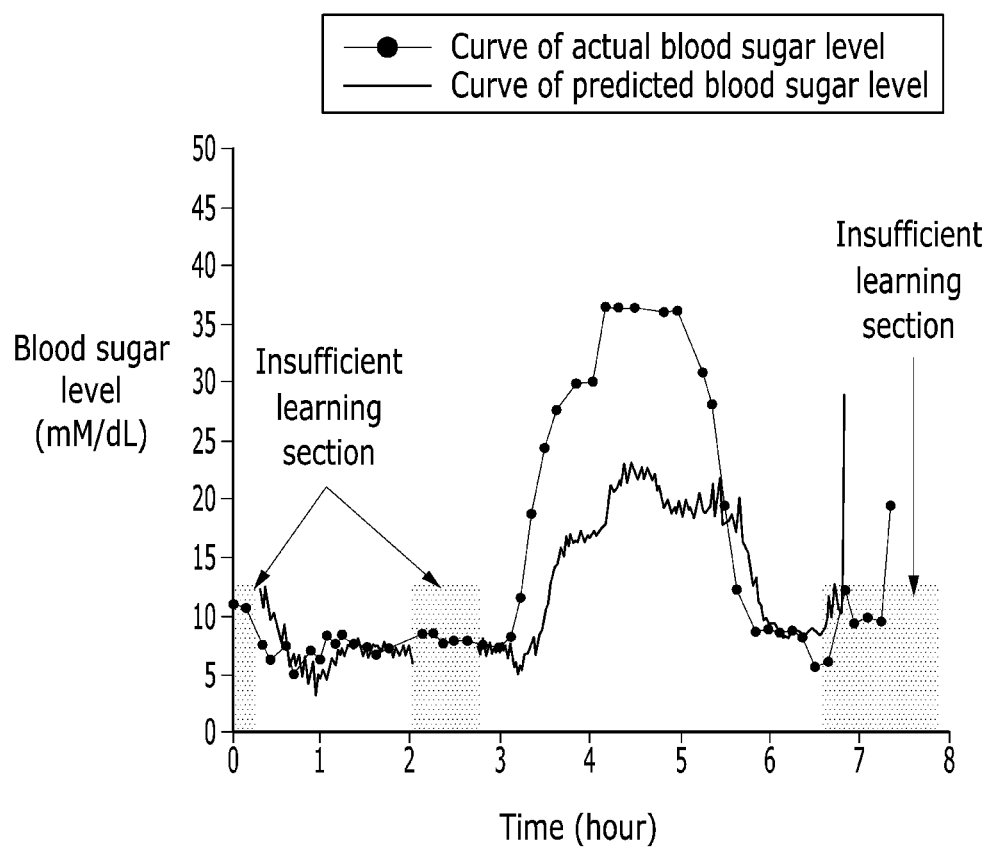
FIG. 11A and FIG. 11B are graphs illustrating a result obtained by predicting a blood sugar level and the actual blood sugar level according to an exemplary embodiment of the invention.
Figure 11B:
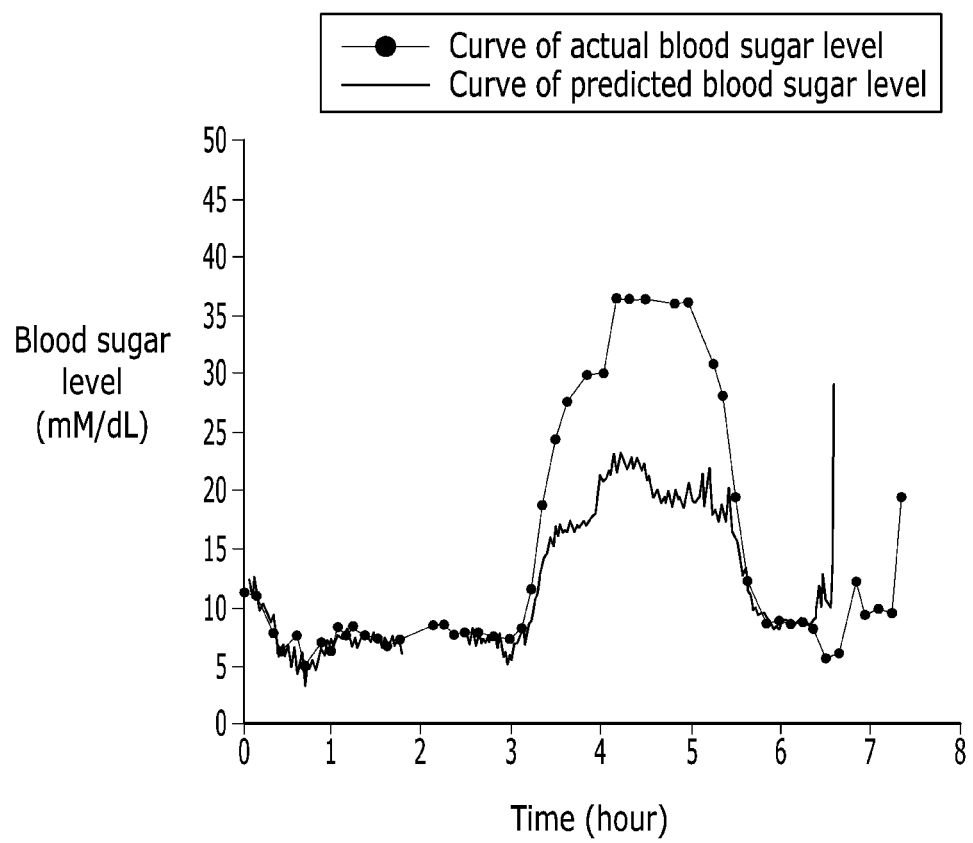

FIG. 11A and FIG. 11B illustrate a result obtained by predicting a blood sugar level and the actual blood sugar level according to an exemplary embodiment of the invention.

In FIG. 11A and FIG. 11B, the horizontal axis represents time, and the vertical axis represents the blood sugar level. The change of a predicted blood sugar level with respect to time and the change of the actual blood sugar level with respect to time are illustrated. In the sections between about zero (0) hour and about 20 minutes, between about 2 hours and about 2.5 hours, and between about 6.5 hours and about 8 hours in FIG. 11A, a blood sugar level may not be effectively predicted due to the insufficiency of the learning section. FIG. 11B illustrates a result of adopting about +15 minutes of a delay to FIG. 11A based on an artery-skin delay in the change of the blood sugar level. That is, since the change of the blood sugar level in the artery is reflected on cutaneous tissue with a delay of about 15 minutes, the result that matches an actual blood-sugar curve in a range of less than about 17 millimoles per deciliter (mM/dL) of the blood sugar level may be acquired as illustrated in FIG. 11B when considering the delay of about 15 minutes.

Figure 12A:
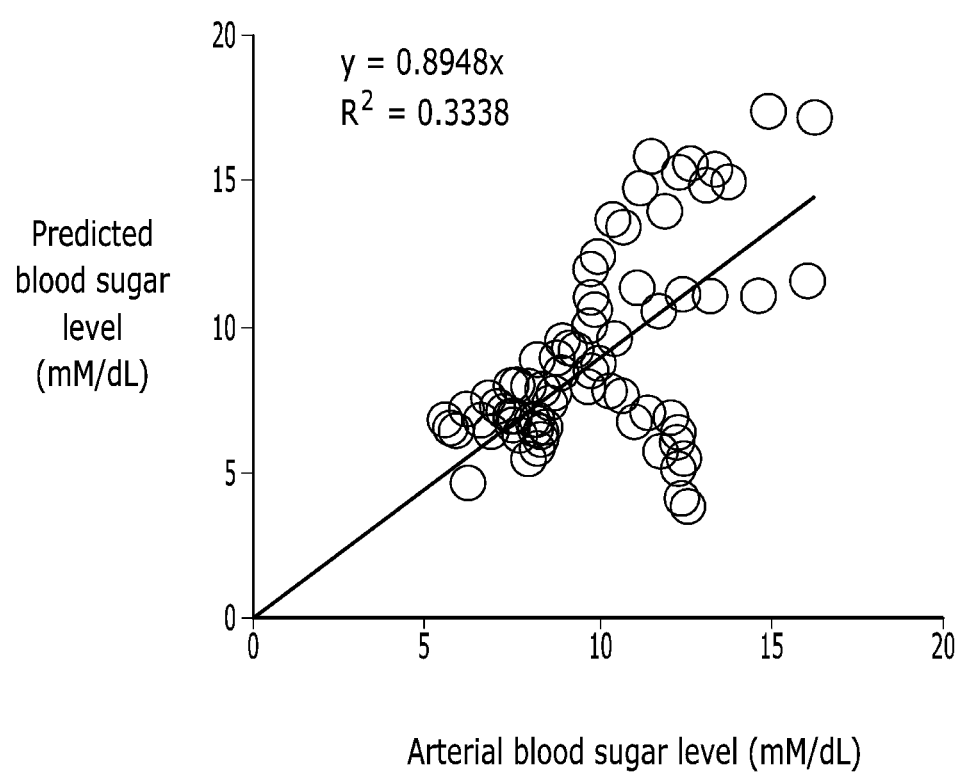
FIG. 12A is a graph illustrating an arterial blood sugar level of a rat in the case that an entire fasting section is determined as a learning section.
Figure 12B:
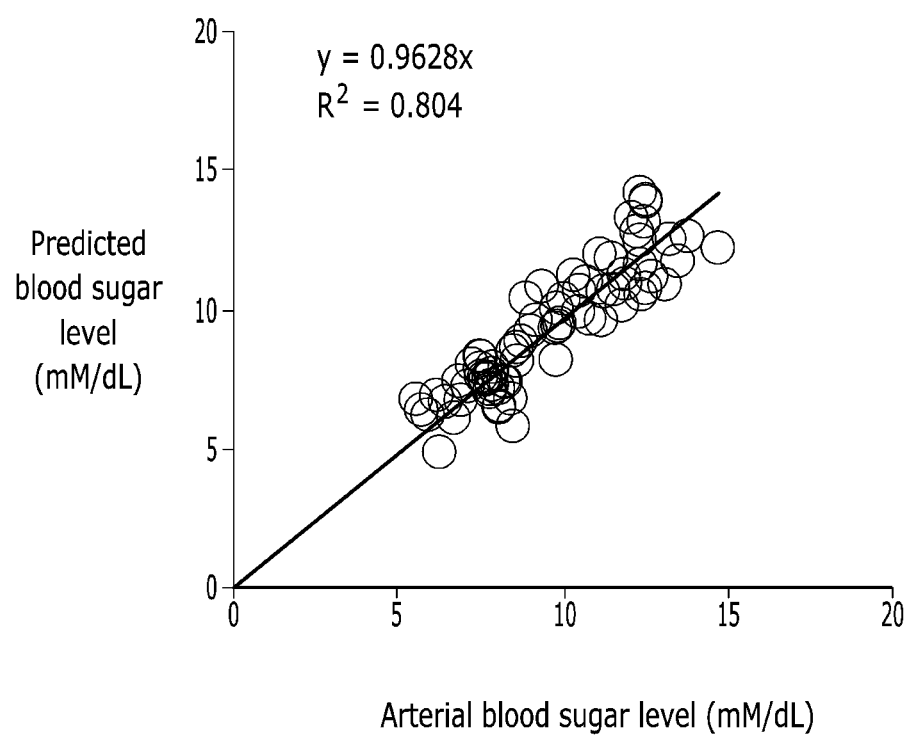
FIG. 12B is a graph illustrating an arterial blood sugar level of the rat predicted by an exemplary embodiment of a concentration predicting apparatus according to an the invention.

FIG. 12A is a graph illustrating an arterial blood sugar level of a rat in the case that an entire fasting section is determined as a learning section, and FIG. 12B is a graph illustrating an arterial blood sugar level of the rat predicted by a concentration predicting apparatus according to an exemplary embodiment of the invention.

The horizontal axes of FIG. 12A and FIG. 12B represent an arterial blood sugar level that are actually measured in the range of less than about 17 mM/dL, and the vertical axes thereof represent the arterial blood sugar level that are predicted in the range of less than about 17 mM/dL. That is, as small circles representing compared results are distributed more tightly to around a x-y line in FIG. 12A and FIG. 12B, predicted arterial blood sugar levels are coincide with actual arterial blood sugar levels, thereby showing an high accuracy of a concentration predicting method according to an exemplary embodiment of the invention.

Referring to FIG. 12A, in a conventional concentration predicting method where the entire fasting section is determined as the learning section, the predicted arterial blood sugar level shows a slight deviation from the actual arterial blood sugar level. However, referring to FIG. 12B, the predicted arterial blood sugar level is considerably coincide with the actual arterial blood sugar level in the range of less than about 17 mM/dL by the result of accurately determining the learning section based on the similar section and the fasting section by the concentration predicting apparatus according to the exemplary embodiment of the invention. That is, FIG. 12B shows that the concentration predicting apparatus according to an exemplary embodiment of the invention may perform a more accurate concentration prediction than that of the conventional concentration predicting method.

Therefore, in such an embodiment, the concentration predicting apparatus for predicting the concentration of the analyte may effectively control the extraneous factor in predicting the concentration of the in vivo analyte by determining the similar section of the spectrum through calculation of the similarity between the in vivo spectrum, and then determining the learning section based on the determined similar section and the section during which the analyte concentration is substantially maintained. In such an embodiment, the concentration predicting apparatus may improve an accuracy of the concentration prediction by predicting the analyte concentration in the similar section including the learning section that is determined by the concentration predicting apparatus.

Figure 13:
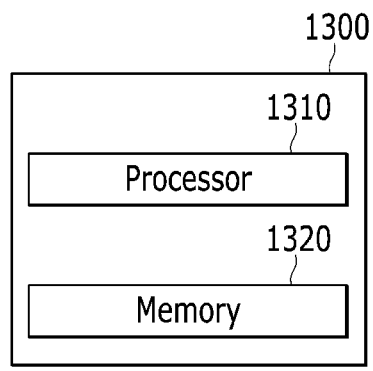
FIG. 13 is a block diagram illustrating an alternative exemplary embodiment of a concentration predicting apparatus for predicting a concentration of an analyte, according to the invention.

FIG. 13 is a block diagram illustrating an alternative exemplary embodiment of a concentration predicting apparatus for predicting a concentration of an analyte, according to the invention.

Referring to FIG. 13, an alternative exemplary embodiment of a concentration predicting apparatus for predicting a concentration of an analyte may be an interactive network analyzing apparatus 1300 including a processor 1310 and a memory 1320. The processor 1310 may be configured to implement the function, the process, or the method of an exemplary embodiment of the invention described herein. The memory 1320 may be connected to the processor 1310 to store diverse information for operating the processor 1310 or may store at least one program performed by the processor 1310. In such an embodiment, the processor 1310 may be configured to operate the interactive network analyzing apparatus 1300.

In an exemplary embodiment of the invention, the memory may be disposed in the interior or exterior of the processor, and may be connected to the processor by various known means. The memory may be one of various volatile and non-volatile storing media. In one exemplary embodiment, for example, the memory may include the ROM or the RAM.

While the invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for predicting a concentration of an in vivo analyte, the method comprising:
    obtaining a plurality of in vivo spectra of the in vivo analyte;
    determining a learning section of a concentration predicting algorithm for the in vivo analyte based on an unchanged section, during which a concentration of the in vivo analyte is not substantially changed, and the in vivo spectra; and
    predicting the concentration of the in vivo analyte by using the concentration predicting algorithm based on a learned result of the learning section and an intrinsic spectrum of the in vivo analyte.

2. The method of claim 1, wherein the in vivo analyte is at least one of glucose, urea, lactate, triglyceride, protein, cholesterol, and ethanol.

3. The method of claim 1, wherein,
    the in vivo analyte is glucose, and
    the unchanged section, during which the concentration of the in vivo analyte is not substantially changed, is a fasting section.

4. The method of claim 1, wherein the in vivo spectrum comprise at least one of an absorption spectrum or a reflection spectrum of an infra-red ray.

5. The method of claim 1, wherein the in vivo spectrum comprise a dispersion spectrum of a single wavelength electromagnetic wave.

6. The method of claim 1, wherein the obtaining the in vivo spectra of the in vivo analyte comprises obtaining the in vivo spectra continually at a predetermined time interval.

7. The method of claim 1, wherein the concentration predicting algorithm comprises a net analyte signal algorithm.

8. The method of claim 1, wherein the determining the learning section comprises:
    calculating a similarity between the in vivo spectra;
    determining a section having a high similarity as a similar section; and
    determining a section, during which the unchanged section and the similar section overlap each other, as the learning section.

9. The method of claim 8, wherein the calculating the similarity between the in vivo spectra comprises:
    aligning baselines of at least two spectra for calculating similarities thereof among the in vivo spectra; and
    calculating a difference between the at least two in vivo spectra, the baselines of which are aligned.

10. The method of claim 1, wherein the predicting the concentration of the in vivo analyte comprises predicting the concentration of the in vivo analyte in the similar section including the learning section when a length of the learning section is longer than a predetermined section length.

11. The method of claim 1, wherein the predicting the concentration of the in vivo analyte comprises re-determining the learning section in the similar section when a length of the learning section is shorter than a predetermined length.

12. The method of claim 1, wherein the predicting the concentration of the in vivo analyte comprises displaying a message to inform a user that a concentration prediction is unavailable when a length of the learning section is shorter than a predetermined length.

13. The method of claim 1, wherein the in vivo analyte is included in a human body, an animal, a mammal, a non-mammal or a microorganism.

14. An apparatus for predicting a concentration of an in vivo analyte, the apparatus comprising:
    a processor; and
    a memory,
    wherein the processor executes a program stored in the memory to perform:
        obtaining a plurality of in vivo spectra of the in vivo analyte;
        determining a learning section for predicting the concentration of the in vivo analyte using a net analyte signal based on an unchanged section, and based on the in vivo spectra, wherein the unchanged section is a time duration during which a concentration of the analyte is not substantially changed, and wherein the determining the learning section comprises:
  calculating similarities between the in vivo spectra;
  determining a section, which has a predetermined similarity, based on the calculated similarities between the in vivo spectra as a similar section; and
  determining a section, during which the unchanged section and the similar section overlap each other, as the learning section; and
predicting the concentration of the in vivo analyte by using the net analyte signal and a spectrum changing factor, which factor is not a function of a change in the concentration of the in vivo analyte, during the learning section and by using an intrinsic spectrum of the in vivo analyte, wherein the intrinsic spectrum is a spectrum of the analyte itself obtained from a sample comprised of the analyte dissolved in an aqueous buffer solution.

15. The apparatus of claim 14, wherein the in vivo analyte is at least one of glucose, urea, lactate, triglyceride, protein, cholesterol, and ethanol.

16. The apparatus of claim 14, wherein
the in vivo analyte is glucose, and
the unchanged section, during which the concentration of the in vivo analyte is not substantially changed, is a fasting section.

17. The apparatus of claim 14, wherein each of the in vivo spectra comprises at least one of an absorption spectrum and a reflection spectrum of an infra-red ray.

18. The apparatus of claim 14, wherein each of the in vivo spectra is obtained by a Raman spectroscopy.

19. The apparatus of claim 14, wherein when the processor performs the obtaining the in vivo spectra of the in vivo analyte, the processor performs:
  obtaining the in vivo spectra repeatedly at a predetermined time interval.

20. The apparatus of claim 14, wherein, when the processor performs the calculating the similarities between the in vivo spectra, the processor performs:
  aligning baselines of at least two in vivo spectra for calculating similarities thereof among the in vivo spectra;
  calculating a difference between the at least two in vivo spectra by aligning baselines of the at least two in vivo spectra; and
  calculating the similarities between the at least two in vivo spectra based on the difference between the at least two in vivo spectra.

21. The apparatus of claim 14, wherein, when the processor performs the predicting the concentration of the in vivo analyte, the processor performs:
  predicting the concentration of the in vivo analyte in the similar section including the learning section, in a case that a length of the learning section is longer than a predetermined section length.

22. The apparatus of claim 14, wherein, when the processor performs the predicting the concentration of the in vivo analyte, the processor performs:
  re-determining the learning section in the similar section, in a case that a length of the learning section is shorter than a predetermined length.

23. The apparatus of claim 14, wherein, when the processor performs the predicting the concentration of the in vivo analyte, the processor performs:
  displaying a message to inform a user that a concentration prediction is unavailable, when a length of the learning section is shorter than a predetermined length.

24. The apparatus of claim 14, wherein the in vivo analyte is included in a human body, an animal, a mammal, a non-mammal, or a microorganism.

25. The apparatus of claim 14 further comprising:
  a communicator which receives the in vivo spectra from an infra-red sensor or a laser sensor through a wired or wireless network.

26. The apparatus of claim 14 further comprising:
  an infra-red sensor which generates the in vivo spectra by radiating an infra-red ray to a human body.

27. The apparatus of claim 14 further comprising: a laser sensor which generates the in vivo spectra by radiating laser light to a human body.

* * * * *